United States Patent
Sadanand

(10) Patent No.: US 10,881,841 B2
(45) Date of Patent: Jan. 5, 2021

(54) SHUNT FLOW MONITOR

(71) Applicant: Siddharth Sadanand, Porter Ranch, CA (US)

(72) Inventor: Siddharth Sadanand, Porter Ranch, CA (US)

(*) Notice: Subject to any disclaimer, the term of this patent is extended or adjusted under 35 U.S.C. 154(b) by 337 days.

(21) Appl. No.: 15/581,975

(22) Filed: Apr. 28, 2017

(65) Prior Publication Data

US 2017/0232240 A1 Aug. 17, 2017

Related U.S. Application Data

(62) Division of application No. 14/208,975, filed on Mar. 13, 2014, now Pat. No. 9,649,481.

(Continued)

(51) Int. Cl.
*A61M 27/00* (2006.01)
*A61B 5/00* (2006.01)
(Continued)

(52) U.S. Cl.
CPC ......... *A61M 27/006* (2013.01); *A61B 5/0031* (2013.01); *A61B 5/031* (2013.01);
(Continued)

(58) Field of Classification Search
CPC .......... A61B 2560/0276; A61B 5/0031; A61B 5/031; A61B 5/4851; A61B 5/686;
(Continued)

(56) References Cited

U.S. PATENT DOCUMENTS 3,769,982 A 11/1973 Schulte
5,935,084 A * 8/1999 Southworth ......... A61B 5/0215
600/561

(Continued)

FOREIGN PATENT DOCUMENTS

DE 19654990 6/1998
EP 2090330 8/2009

OTHER PUBLICATIONS

PCT Search Report and Written Opinion dated Aug. 29, 2014, PCT Appln. No. PCT/US2014/027387, 13 pages.

(Continued)

*Primary Examiner* — Kai H Weng
(74) *Attorney, Agent, or Firm* — Womble Bond Dickinson (US) LLP

(57) ABSTRACT

A shunt including an implantable housing having a proximal end and a distal end. A pressure sensitive valve is contained within the housing at a position between the proximal end and the distal end, and the pressure sensitive valve is capable of controlling a flow of fluid between the fluid inlet port and the fluid outlet port. The shunt further including a sensor assembly fluidly coupled to the pressure sensitive valve, wherein the sensor assembly is mechanically actuated and capable of detecting the flow of fluid through the pressure sensitive valve. A condition of the shunt can be detected by detecting a flow of fluid through the shunt and generating a signal indicative of a period of fluid flow through the implantable shunt based on the detecting. The signal can be output to an external device capable of determining, from the signal, whether the shunt is malfunctioning.

19 Claims, 14 Drawing Sheets

Related U.S. Application Data

(60) Provisional application No. 61/784,616, filed on Mar. 14, 2013.

(51) Int. Cl.
*A61B 5/03* (2006.01)
*G01F 1/075* (2006.01)
*A61M 39/22* (2006.01)

(52) U.S. Cl.
CPC ............ *A61B 5/4851* (2013.01); *A61B 5/686* (2013.01); *A61M 39/22* (2013.01); *G01F 1/075* (2013.01); *A61B 2560/0276* (2013.01); *A61M 2027/004* (2013.01); *A61M 2205/3331* (2013.01); *A61M 2205/3334* (2013.01); *A61M 2205/3592* (2013.01); *A61M 2205/50* (2013.01)

(58) Field of Classification Search
CPC .... A61M 2027/004; A61M 2205/3331; A61M 2205/3334; A61M 2205/3592; A61M 2205/50; A61M 27/006; A61M 39/22
See application file for complete search history.

(56) References Cited

U.S. PATENT DOCUMENTS

| | | | |
|---|---|---|---|
| 6,391,019 | B1 | 5/2002 | Ito |
| 8,123,714 | B2 | 2/2012 | Ludin et al. |
| 2004/0068221 | A1* | 4/2004 | Silverberg .......... A61M 27/006 604/9 |
| 2004/0147871 | A1 | 7/2004 | Burnett |
| 2004/0260229 | A1* | 12/2004 | Meir ...................... A61B 5/031 604/9 |
| 2009/0005720 | A1* | 1/2009 | Ludin ................. A61M 27/006 604/9 |
| 2009/0107233 | A1 | 4/2009 | Kassem |
| 2009/0112308 | A1* | 4/2009 | Kassem ............... A61B 5/0031 623/1.24 |
| 2010/0076366 | A1 | 3/2010 | Henderson, Sr. et al. |
| 2012/0232461 | A1* | 9/2012 | Seaver ................ A61M 27/006 604/9 |
| 2012/0302874 | A1* | 11/2012 | Hollstien ............. A61B 5/0084 600/424 |

OTHER PUBLICATIONS

Final Office Action dated Oct. 3, 2016, U.S. Appl. No. 14/208,975.
"Strata Shunt System for Normal Pressure Hydrocephalus", Dept. of Neurological Surgery of Univ. of Pittsburgh, accessed via Internet at bing.com on Mar. 1, 2012, 2 pages.
Kurtom, Khalid H., et al., "Siphon Regulatory Devices: Their Role in the Treatment of Hydrocephalus: Cerebrospinal Fluid Siphoning Pathophysiologies", Neurosurg Focus, 22(4), accessed via Internet at medscape.com on Apr. 24, 2012, (2007), 7 pages.
Shellock, Frank G., et al., "Cerebrospinal Fluid (CSF) Shunt Valves and Accessories", accessed via Internet at mrisafety.com on Mar. 1, 2012, (2012).

\* cited by examiner

SHUNT FLOW MONITOR

CROSS-REFERENCE TO RELATED APPLICATION

The application is a divisional of co-pending U.S. patent application Ser. No. 14/208,975, filed Mar. 13, 2014, which claims the benefit of the earlier filing date of U.S. Provisional Patent Application No. 61/784,616, filed Mar. 14, 2013 and incorporated herein by reference.

BACKGROUND

Field

A method and apparatus for detecting a condition of an implantable shunt device, more specifically, for detecting a location of a shunt malfunction. Other embodiments are also described and claimed.

Background

A shunt is a surgically implanted device that allows for movement of fluid from one part of the body to another. In the case of a cerebral shunt, the shunt diverts cerebrospinal fluid (CSF) from the brain or spine into various body cavities such as the peritoneum, pleural space, heart, etc. CSF is produced by the brain and circulates from the brain to the spine and then gets absorbed in the veins. A normal adult produces between 15-20 cc of CSF per hour. CSF acts as a "cushion" or buffer for the cortex, providing a basic mechanical and immunological protection to the brain inside the skull and serves a vital function in cerebral autoregulation of cerebral blood flow.

When the body fails to properly absorb the CSF, an abnormal accumulation of CSF occurs in the ventricles or cavities within the brain resulting in a medical condition known as hydrocephalus. A cerebral shunt may be implanted within the patient's brain to help drain the CSF and redistribute it to a different body region for absorption. Cerebral shunts typically consist of three parts: a proximal catheter, a valve and a distal catheter. The proximal catheter is inserted into the brain ventricle, which is a site of CSF build up, while the distal catheter is positioned within any body tissue having enough epithelial cells to absorb the incoming CSF. Typically, the distal catheter is positioned within the peritoneum (where the abdominal organs are located) or the pleural space outside the lungs or the atrium of the heart. The pressure differential between the high pressure brain region and the lower pressure abdomen, lung or atrial region causes the CSF to be drawn into the proximal catheter and out the end of the distal catheter.

The valve is between the proximal catheter and the distal catheter and is typically positioned behind the ear. The valve is used to control the amount of CSF flowing from the brain to the stomach. When a pressure within the brain increases, a pressure level at the valve increases above a threshold level (e.g., a low, medium or high pressure) causing a gate within the valve to open. CSF can then flow from the brain to the abdomen thereby reducing the pressure level within the brain. Once the pressure drops below the threshold level at the gate, the valve closes the gate so that CSF flow is stopped. In a fixed pressure setting valve, the pressure threshold level of the valve may be preset prior to placement of the shunt within the body. Alternatively, the valve may be adjustable such that the threshold level can be changed electronically using a device outside the body without having to remove the shunt.

A working cerebral shunt is critical to patient survival. Cerebral shunts, however, often fail. The failure can be either mechanical or infectious. In addition, a patient may report symptoms consistent with shunt failure, but in actuality, the shunt is working fine. Since the shunt is implanted within the patient's body, it is difficult to determine the condition of the shunt and, when there is a failure, which part of the stunt requires repair. A computed tomography (CT) scan can be performed to determine whether the brain is draining properly, but sometimes a CAT scan is inconclusive because the desired region cannot be viewed properly. In addition, the portion of the shunt in need of repair cannot typically be identified from the CAT scan and CSF flow cannot be evaluated. Similar problems arise using x-ray techniques. Other techniques to assess CSF flow through the shunt, such as a radionuclide shuntogram or needle aspiration of the valve reservoir are invasive, unreliable and non-informative. The patient must therefore undergo an exploratory shunt surgery so that the surgeon can examine the shunt directly. Exposing the shunt, however, comes with subjecting the patient to surgical risks and, in addition, a high infection risk to the patient. In particular, each time a shunt is exposed, there is a 30% chance that within 3 months the patient will get an infection.

BRIEF DESCRIPTION OF THE DRAWINGS

The following illustration is by way of example and not by way of limitation in the figures of the accompanying drawings in which like references indicate like elements. It should be noted that references to "an" or "one" embodiment in this disclosure are not necessarily to the same embodiment, and such references mean at least one.

DETAILED DESCRIPTION

In this section we shall explain several preferred embodiments with reference to the appended drawings. Whenever the shapes, relative positions and other aspects of the parts described in the embodiments are not clearly defined, the scope of the embodiments is not limited only to the parts shown, which are meant merely for the purpose of illustration. Also, while numerous details are set forth, it is understood that some embodiments may be practiced without these details. In other instances, well-known structures and techniques have not been shown in detail so as not to obscure the understanding of this description.

Figure 1:
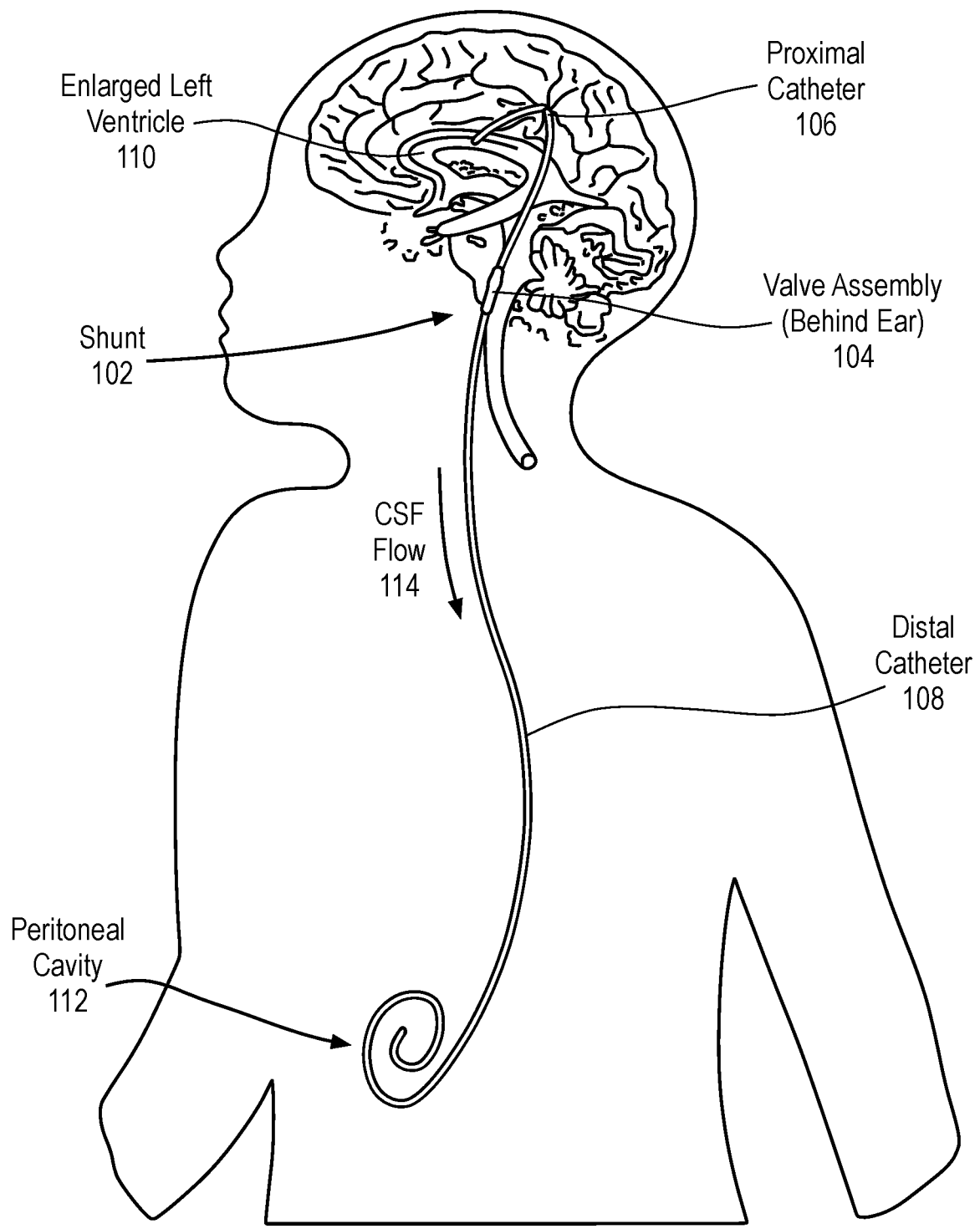
FIG. 1 illustrates a side cross-sectional view of a shunt implanted within a subject.

FIG. 1 illustrates a side cross-sectional view of a shunt implanted within a subject. Cerebral shunt 102 generally includes a valve assembly 104 connected at a proximal end to proximal catheter 106 and a distal end to distal catheter 108. The valve assembly 104 is typically implanted behind the subject's ear. The proximal end of proximal catheter 106 is positioned within an enlarged ventricle 110 of the subject and the distal end is connected to valve assembly 104. The proximal end of distal catheter 108 is connected to the distal end of valve assembly 104 and the distal end of distal catheter 108 is positioned within the peritoneal cavity 112 of the subject. Excess CSF is drawn up into the proximal end of proximal catheter 106, flows through valve assembly 104 and drains out the distal end of distal catheter 108 into peritoneal cavity 112. The direction of CSF flow is illustrated by arrow 114. Although distal catheter 108 is shown positioned within peritoneal cavity 112, it may also be positioned within another body cavity capable of absorbing CSF.

Figure 2:
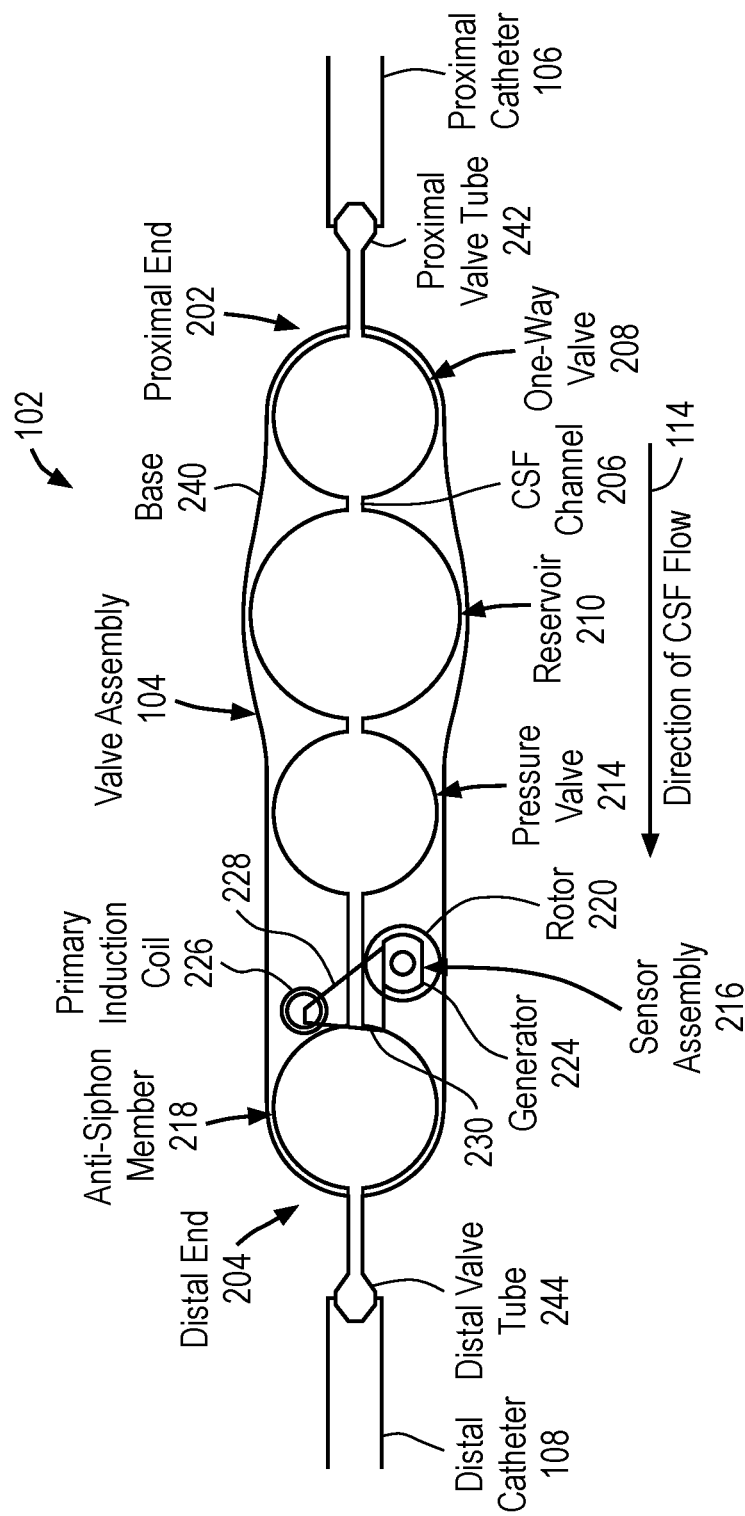
FIG. 2 illustrates a plan view of the shunt illustrated in FIG. 1.

FIG. 2 illustrates a plan view of the shunt illustrated in FIG. 1. Shunt 102 includes valve assembly 104, proximal catheter 106 and distal catheter 108. Proximal catheter 106 is fluidly connected to proximal end 202 of valve assembly 104 by proximal valve tube 242. Similarly, distal catheter 108 is fluidly connected to distal end 204 of valve assembly 104 by distal valve tube 244. Proximal valve tube 242 and distal valve tube 244 help to regulate CSF flow into and out of valve assembly 104. Representatively, each of proximal valve tube 242 and distal valve tube 244 may be one-way valves that are one way in a direction of CSF flow 114.

Valve assembly 104 includes an outer housing formed by a base member 240 and a cover member (removed for illustration purposes). Base member 240 includes channel 206 formed along its length from the proximal end 202 to the distal end 204. CSF flowing into valve assembly 104 from proximal valve tube 242 flows through channel 206 in the direction of arrow 114 to the distal end 204 of valve assembly 104. Channel 206 may have any size and dimensions suitable for accommodating a desired amount of CSF flow.

Valve assembly 104 further includes one-way valve 208, reservoir 210, pressure valve 214, sensor assembly 216 and anti-siphon member 218 mounted along base member 240. Each of these components is in fluid communication with channel 206 and help to regulate and/or monitor CSF flow through valve assembly 104.

In one embodiment, one-way valve 208 may be an optional valve positioned at the proximal end 202 of valve assembly 104. One-way valve 208 may be any type of one-way valve capable of allowing CSF to flow into valve assembly 104 in a direction of CSF flow 114 and preventing CSF flow in an opposite direction.

Reservoir 210 may be at a position downstream from one-way valve 208 along CSF channel 206. Reservoir 210 serves several important functions. Reservoir 210 can be used to remove samples of CSF for testing using a needle or a syringe. Fluids may also be injected into reservoir 210 and flushed through valve assembly 104 to test for flow and ensure proper functioning of shunt 102. Reservoir 210 may therefore be formed of any material that can be pierced by a needle or syringe, for example a polymer material. In one embodiment, reservoir 210 may be a bulb shaped structure formed of a rubber material.

Pressure valve 214 may be at a position downstream from reservoir 210, also along CSF channel 206. Pressure valve 214 may be used to moderate the pressure or flow rate of CSF through valve assembly 104. Pressure valve 214 may be any type of pressure valve suitable for use in a shunt system. For example, pressure valve 214 may be a high pressure, medium pressure, low pressure or low-low pressure valve such as those commercially available from Medtronic Inc. Pressure valve 214 may be programmable, meaning that its pressure settings can be changed remotely after implantation or fixed, meaning that its pressure settings are fixed once implanted within the body. Pressure valve 214 includes a gate which, at a certain threshold pressure, either opens to allow CSF flow or closes to prevent CSF flow through valve assembly 104. For example, when the CSF pressure within valve assembly 104 is above a predetermined threshold value, the gate opens so that CSF can flow through pressure valve 214 and out distal end 204 of valve assembly 104. CSF flow through pressure valve 214 reduces the pressure within valve assembly 104. Once the pressure is below the set threshold, the gate closes and CSF flow to the distal end 204 stops.

Anti-siphon member 218 is positioned at the distal end 204 of valve assembly 104. Anti-siphon member 218 may be optional, and when included, may be any type of anti-siphoning device capable of preventing CSF from being drawn into valve assembly 104 through the distal end.

Sensor assembly 216 is positioned between pressure valve 214 and anti-siphon member 218. In this aspect, sensor assembly 216 is distal to or downstream from pressure valve 214. Sensor assembly 216 can therefore detect CSF flow through pressure valve 214. In this aspect, sensor assembly 216 can be used to indirectly monitor the activity of pressure valve 214. The activity of pressure valve 214 can be used to identify a location of any malfunctions within shunt 102 as will be described in more detail in reference to FIG. 6 to FIG. 12.

Sensor assembly 216 is designed so that information corresponding to the activity of pressure valve 214, and in turn a condition of shunt 102, can be obtained by the care provider transdermally (a non-invasive method). This provides advantages over current detection procedures. In particular, as previously discussed, shunt malfunction is difficult to confirm non-invasively and it is even more difficult to identify which portion of the shunt is malfunctioning without performing an exploratory surgical procedure. These exploratory surgical procedures are not only invasive and uncomfortable for the patient subjecting the patient to surgical risks, they significantly increase the likelihood of patient infection including but not limited to meningitis.

Sensor assembly 216 therefore provides invaluable information in a non-invasive manner, which significantly reduces patient risks. Moreover, in one embodiment, sensor assembly 216 is mechanically actuated, in other words it is actuated by rotation of rotor assembly 220 and does not require a battery for operation. Since sensor is mechanically actuated, surgical intervention to replace a battery associated with the shunt is avoided. It is contemplated, however, that in some embodiments, a battery may be used to actuate one or more of valve assembly 104 components. In another embodiment described in reference to FIG. 15A and FIG. 15B, a microprocessor recording and an RFID detection mechanism may be used for this purpose.

Sensor assembly 216 will now be described in detail. In one embodiment, sensor assembly 216 includes a rotor assembly 220, a generator assembly 224 and a primary induction coil 226. The rotor assembly 220 is rotatably coupled to base member 240 and is within the flow path of CSF flowing through channel 206. As CSF flows in direction 114 through channel 206, rotor assembly 220 rotates. Rotation of rotor assembly 220 causes a rotor (not shown) within generator assembly 224 to rotate. Generator assembly 224 converts this mechanical energy into an electrical pulse, which is transmitted through one or more of conducting wires 228, 230 to primary induction coil 226, also mounted on base member 240. Primary induction coil 226 generates a magnetic pulse corresponding to the electrical pulse output by generator assembly 224. This magnetic pulse is then detected through transdermal coupling by a secondary induction coil positioned within an external device.

Figure 5A:
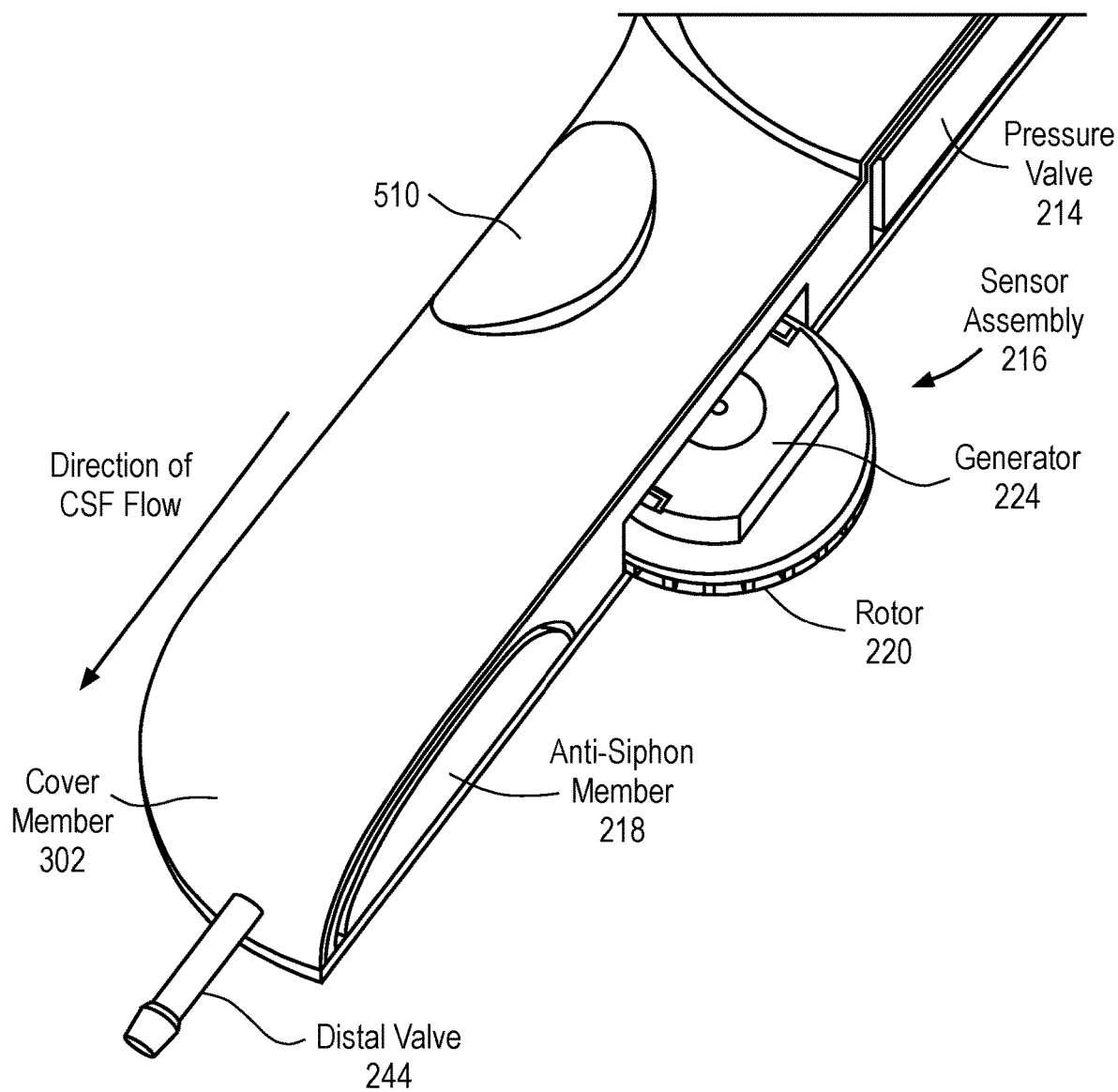
FIG. 5A illustrates a perspective cut out view of one embodiment of a valve assembly.
Figure 5B:
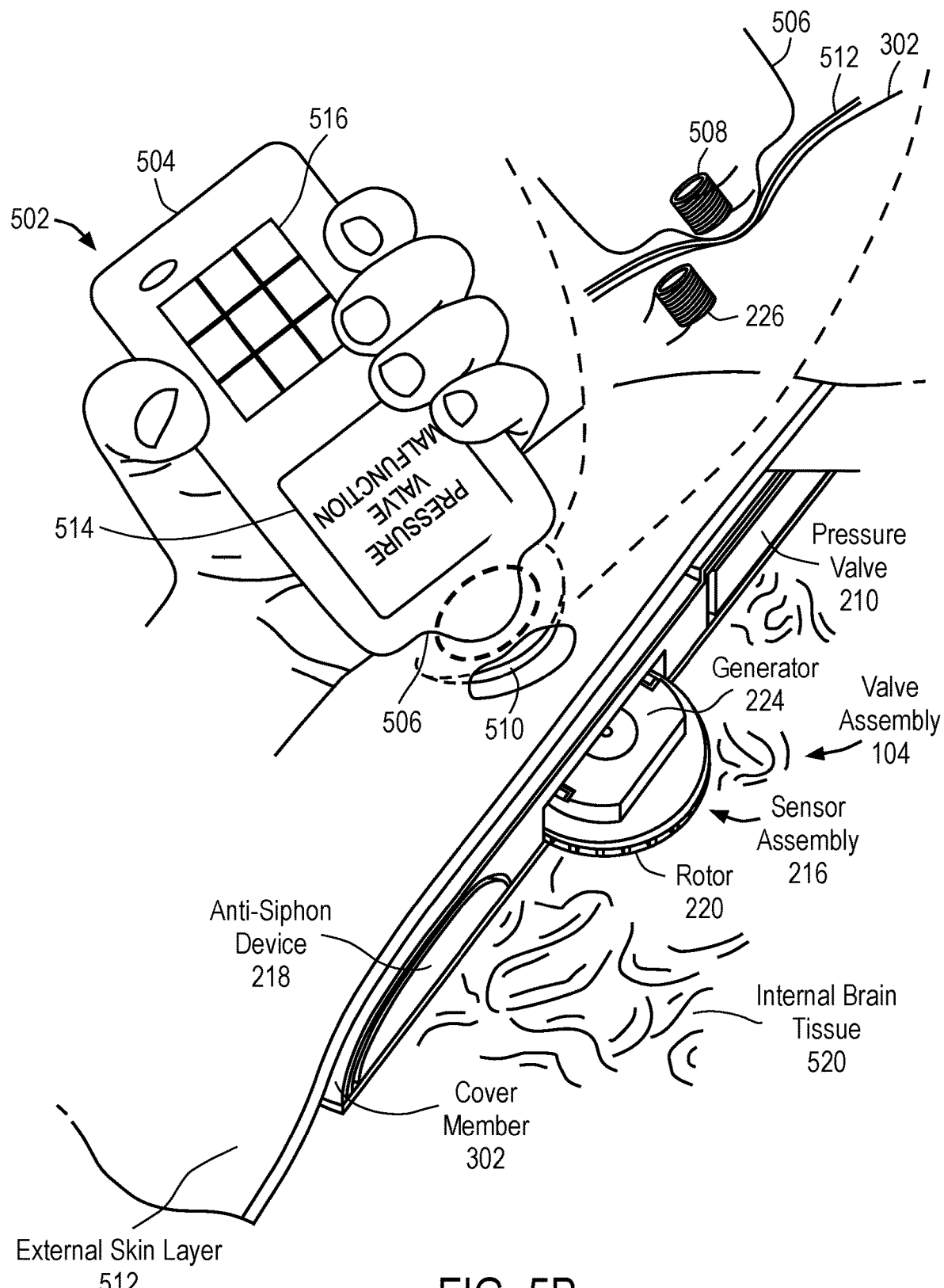
FIG. 5B illustrates a perspective cut out view of one embodiment of a valve assembly implanted within a patient.

The external device may be, for example, a hand-held signal processing member as will be described in more detail in reference to FIG. 5B. The hand-held signal processing member may be any external electronic device capable of processing one or more signals output by sensor assembly 216, processing the signal and displaying to a user whether a malfunction in the shunt has occurred and if so, the location of the malfunction. For example, the external device may be any type of mobile device having a display capable of displaying information to the user.

Alternatively, the external device may simply detect the signals output by sensor assembly 216 and transmit the signals to a separate display and/or computing device that can display the shunt condition. For example, the external device may be a probe, or similar device, that is connected to a patient monitor capable of displaying information to the care provider. When the probe, which contains the secondary induction coil, is transdermally coupled to the shunt, it reads the signal output by sensor assembly 216 and transmits it to the display device. The display device may be, for example, a computer, having a processing program that can process signals from the probe and display the associated shunt condition information on the display.

It is noted that although in one embodiment, sensor assembly 216 is positioned between pressure valve 214 and anti-siphon member 218, it may be positioned at other regions of valve assembly 104 to monitor fluid flow through valve assembly 104. For example, sensor assembly 216 could be positioned proximal to pressure valve 214. In any case, since the position of sensor assembly 216 relative to the other valve assembly components 104 is known, the output signal can be evaluated and interpreted to determine a condition of shunt 102, and in particular, a location of a malfunction.

Figure 3:
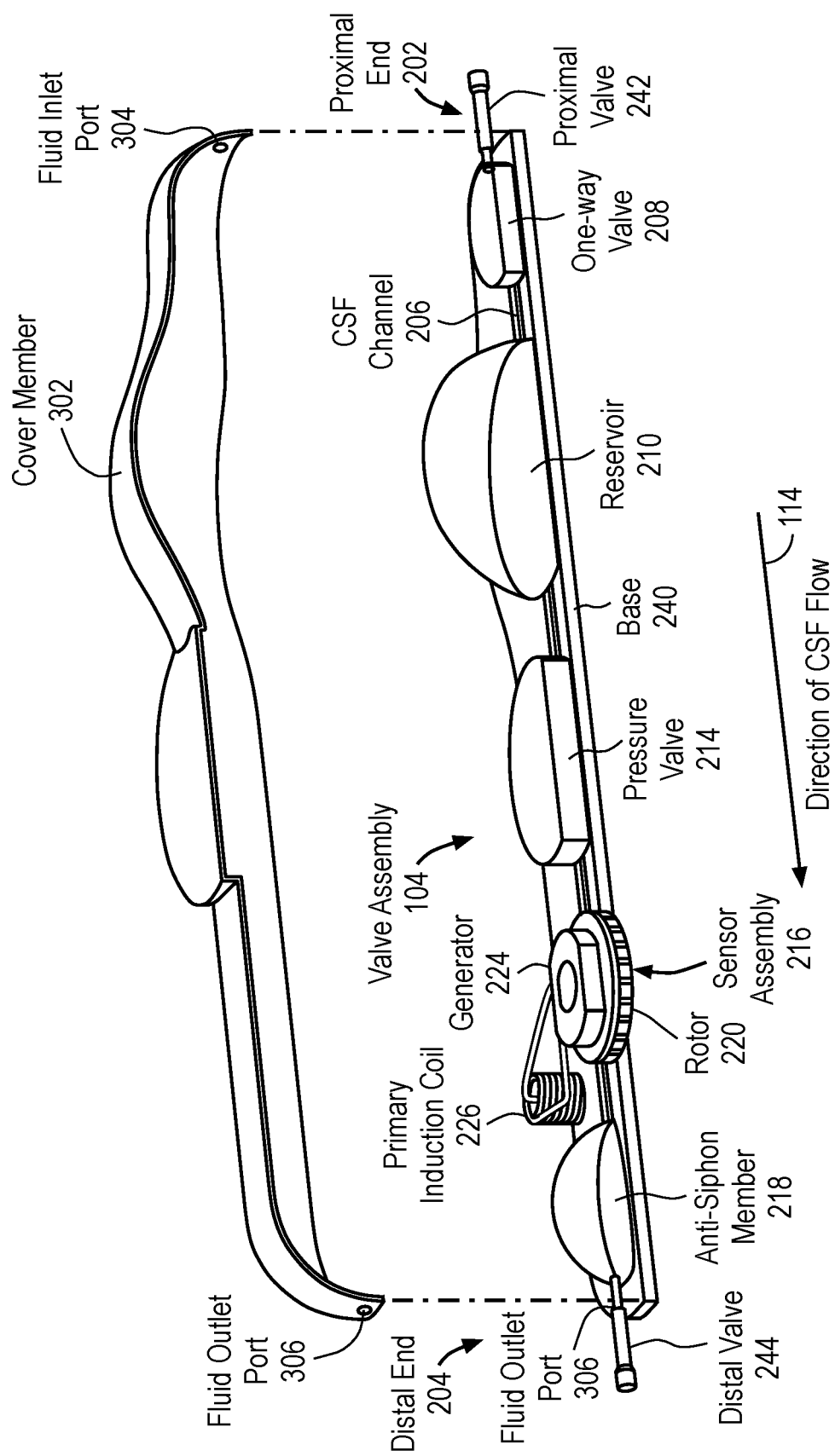
FIG. 3 illustrates a side perspective cut out view of the valve assembly of FIG. 2.

FIG. 3 illustrates a side perspective cut out view of the valve assembly of FIG. 2. Cover member 302 is shown removed from base member 240 so that the internal components can be viewed. When cover member 302 is attached to base member 240, the two structures form a housing that encases each of the components attached to base 240. Fluid inlet port 304 may be formed in proximal end 202 and fluid outlet port 306 formed in the distal end 204. The tube portion of proximal valve tube 242 may enter the housing through fluid inlet port 304 and connect to one-way valve 208. Distal valve tube 244 enters the housing through fluid outlet port 306 and connects to anti-siphon member 218. CSF from proximal catheter 106 enters valve assembly 104 through fluid inlet port 304 to one-way valve 208. One-way valve 208 outputs the CSF into channel 206. CSF flows along channel 206 to reservoir 210, pressure valve 214, sensor assembly 216 and finally to anti-siphon member 218. Anti-siphon member 218 outputs CSF through distal valve tube 244 within fluid outlet port 306 so that it can travel through distal catheter 108 to the desired body cavity.

In some embodiments, fluid inlet port 304 and/or fluid outlet port 306 are holes formed entirely through the wall of cover member 302. In other embodiments, fluid inlet port 304 and/or fluid outlet port 306 are slots formed along the bottom edge of cover member 302. When cover member 302 is placed on base member 240, the holes or slots align with channel 206 so that fluid can enter valve assembly 104 and flow along channel 206 from the proximal end 202 to the distal end 204.

Figure 4:
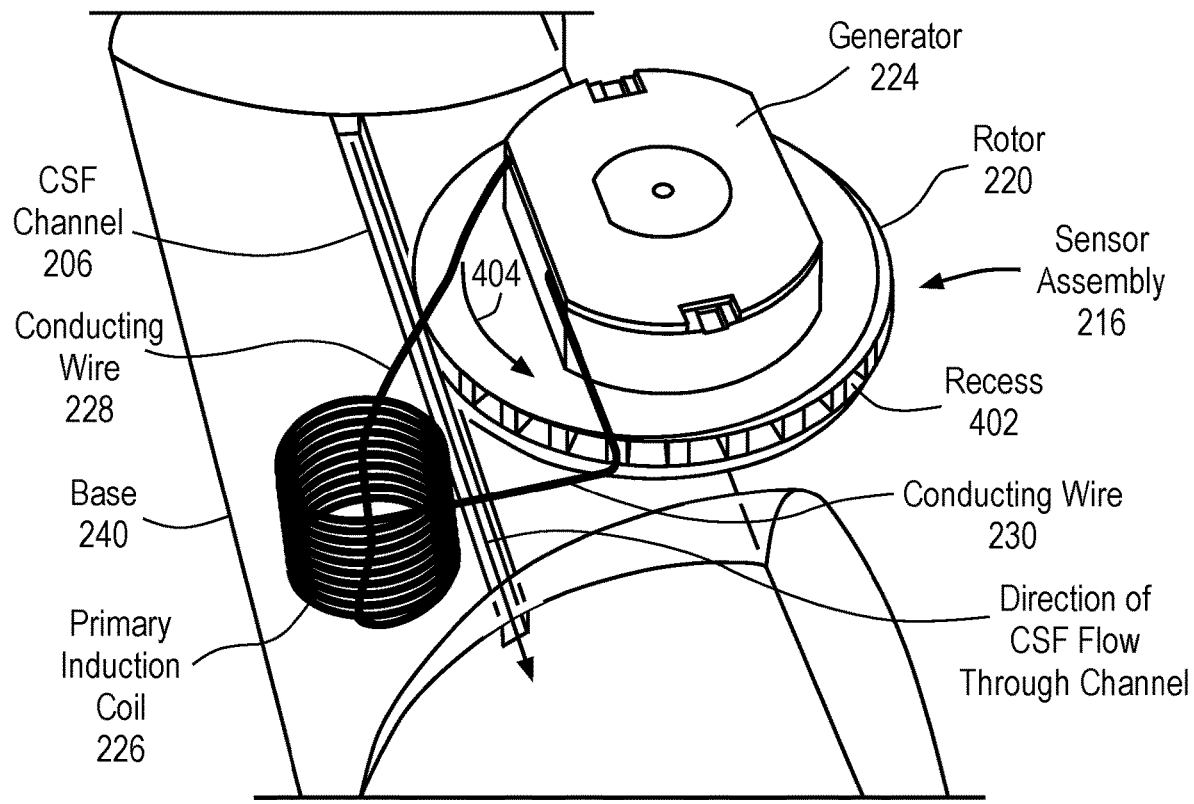
FIG. 4 illustrates a perspective view of one embodiment of a sensor assembly.

FIG. 4 illustrates a perspective view of one embodiment of a sensor assembly. As previously discussed, sensor assembly 216 may include rotor assembly 220 connected to generator assembly 224, which is in turn connected to primary induction coil 226. Rotor assembly 220 may be a substantially planar, disc shaped structure having recesses 402 around its circumferential wall. Rotor assembly 220 is mounted along base member 240 so that CSF flowing though channel 206 catches on recesses 402 causing rotor assembly 220 to rotate in the direction of CSF flow as illustrated by arrow 404. It is noted that the bearings used to mount rotor assembly 220 are outside of CSF flow therefore preventing malfunction of rotor assembly 220 due to CSF build up about the bearings.

Rotor assembly 220 is mechanically connected to generator assembly 224 such that rotation of rotor assembly 220 drives rotation of a rotor within generator assembly 224. Generator assembly 224 outputs this mechanical energy as an electrical pulse or voltage. This electrical pulse is transmitted through one or more of conducting wires 228, 230 to primary induction coil 226. Primary induction coil 226 generates a magnetic pulse corresponding to the electrical pulse output by generator assembly 224. Accordingly, for every electrical pulse output by generator assembly 224, a corresponding magnetic pulse or signal is output by primary induction coil 226.

This magnetic pulse is then detected through transdermal coupling by a secondary induction coil positioned within an external device. To facilitate coupling and alignment of primary induction coil 226 with the external secondary induction coil, cover member 302 may have a recess portion 510 formed within a portion of the outer wall as illustrated in FIG. 5A. Recess portion 510 may be positioned near primary induction coil 226. When external device 502 is positioned within recess portion 510, as illustrated in FIG. 5B, secondary induction coil 508 is substantially aligned with primary induction coil 226. In this aspect, recess portion 510 may be of any size and shape capable of aligning primary induction coil 226 with secondary induction coil 508.

To further facilitate alignment, secondary induction coil 508 may be positioned within a portion of external device 502 that is complimentary to, and can easily be aligned within, recess portion 510. Representatively, external device 502 may be formed by a housing 504 having a protruding portion 506 complementary to the shape of recess portion 510 so that it can rest within recess portion 510. When valve assembly 104 is implanted between the external skin layer 512 and the internal brain tissue 520, the user can digitally examine the valve assembly 104 and identify recess portion 510 through external skin layer 512. Once recess portion 510 is identified, pressing of external device 502 against recess portion 510 ensures that primary induction coil 226 and secondary induction coil 508 are properly aligned.

As previously discussed, the external device may include a signal processing member that can process the signals output by sensor assembly 216 and identify to a user whether a malfunction in the shunt has occurred and if so, the location of the malfunction. In this aspect, hand-held device may include display 514 to display the processing results in any number of ways. In one embodiment, display 514 may be an LCD alphanumeric display or any other type of display capable of communicating a malfunction to a user. For example, display 514 may indicate that the shunt is malfunctioning and/or may identify the specific location of the malfunction. Representatively, display 514 may indicate to the user that the malfunction is at the location of any of the internal components. For example, display 514 can indicate to the user that the proximal catheter is blocked, the distal catheter is blocked or that the pressure valve is malfunctioning, for example, the valve setting is too low or too high. It should further be understood that any signals (also referred to as information or communications herein) output by sensor assembly 216 and/or information as to whether a malfunction has occurred may be recorded and stored for later analysis.

It is further contemplated that in some embodiments the external device could be a patch connected to a lead, which is in turn connected to a non-mobile or mobile computing device, such as device 502. Representatively, the patch may have an adhesive side which sticks to the external skin layer 512 at a position near recess portion 510 and the opposite side may be connected to a lead. The signals output by sensor assembly 216 may be transmitted along the lead to the associated computing device for processing and, in some cases, recording. In this aspect, the shunt condition may be continuously or periodically monitored without the presence of a health care provider and/or someone to manually align and hold the device near sensor assembly 216 when monitoring is required.

The algorithms for identifying an overall condition of the shunt and/or malfunction from the signals output by the sensor assembly 216 will now be discussed in reference to FIG. 6-FIG. 12.

As previously discussed, pressure valve 214 has a predetermined pressure threshold and therefore controls whether CSF flows through valve assembly 104. If pressure valve 214 has a low threshold setting, it may only take a relatively low pressure for pressure valve 214 to open and allow CSF flow. Alternatively, pressure valve 214 may have a high threshold setting such that a relatively high pressure is required to open pressure valve 214 and allow CSF flow. Sensor assembly 216 is positioned downstream from pressure valve 214, in other words between pressure valve 214 and distal end 204. Thus, any CSF flow through pressure valve 214, or a lack of fluid flow, is detected and monitored by sensor assembly 216. Sensor assembly 216 outputs a corresponding signal that can be detected by secondary induction coil 508 within external device 502. The signal detected by secondary induction coil 508 may be represented as a square waveform that is indicative of the presence of CSF flow distal to pressure valve 214 and the length of time the fluid is flowing. The square waveform, and/or the information used to generate the square waveform, may be used to determine a shunt malfunction by comparing the waveform and/or information to a control. The control may be specific to a particular patient or may be a standardized control preprogrammed into the external device during a manufacturing operation. In the case of a control specific to the patient, the control values may be determined shortly after shunt placement within the patient and then saved for future use.

Figure 6:
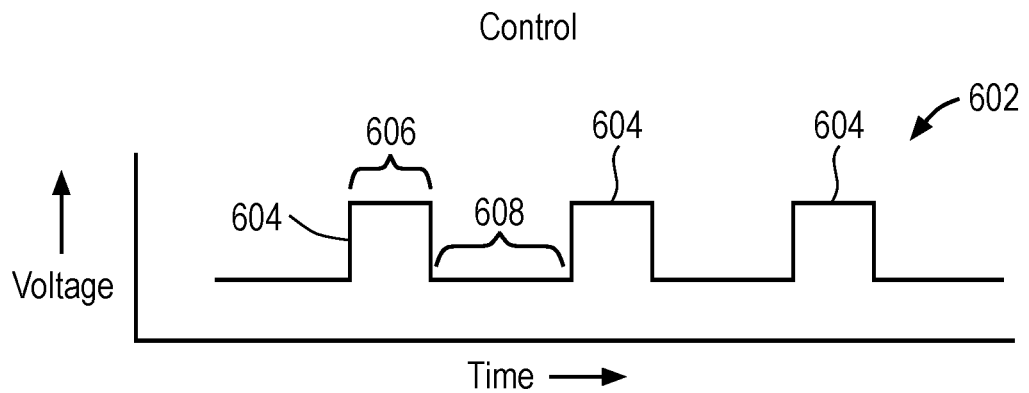
FIG. 6 illustrates a control waveform indicative of a properly functioning shunt.

FIG. 6 illustrates a control CSF waveform indicative of a properly functioning shunt. The y-axis represents a voltage measurement and the x-axis represents time. Each wave 604 represents a voltage increase caused by CSF flow past sensor assembly 216. CSF flows past sensor assembly 216 when pressure valve 214 is open. Thus, the period of time over which wave 604 occurs, in other words the width of wave 604, is proportional to the length of time pressure valve 214 remains open. This period 606 within which pressure valve 214 remains open may be referred to herein interchangeably as the wave period, the open valve period, the fluid flow period or the wave width. Thus, the longer pressure valve 214 remains open, the wider wave 604 will be.

Area 608 between waves 604 represents a substantially zero or low voltage area which corresponds to the period of time over which no CSF is flowing past sensor assembly 216, in other words, pressure valve 214 is closed and no CSF is flowing through the valve. Area 608 may be referred to herein interchangeably as the period between waves, between wave period, the closed valve period, the no-flow period or zero or low voltage period. The wave period 606 along with the between wave period 608 can be used to indirectly evaluate the activity of pressure valve 214 and in turn, a condition of the shunt. Waveform 602 is a control waveform indicative of a properly functioning shunt that is allowing for CSF flow at consistent and regular intervals.

Figure 7:
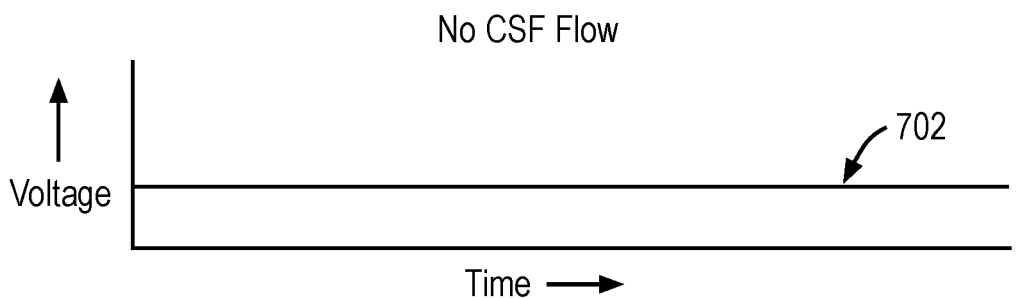
FIG. 7 illustrates a waveform indicative of a shunt in which no CSF is flowing through the pressure valve.

FIG. 7 illustrates a CSF waveform indicative of a shunt in which no CSF is flowing through the pressure valve. In particular, waveform 702 has a constant substantially zero or low voltage. The constant zero or low voltage indicates one of two scenarios. The first being that there is a complete blockage of the shunt, i.e., no CSF is flowing through the shunt therefore pressure valve 214 remains closed. Alternatively, the constant zero or low voltage could indicate that CSF production is below the threshold of pressure valve 214 and therefore pressure valve 214 remains closed. The external device 502 can display to the user that one of the two scenarios is occurring. The user can then use this information to determine the appropriate course of action. For example, the user may decrease the pressure valve threshold so that a lower CSF pressure is required to open pressure valve 214. After a period of time, the user can then take a second reading. If the second reading results in a waveform more consistent with the control waveform 602, the user can determine that it was the threshold setting that needed to be adjusted. If the reading remains the same, in other words pressure valve 214 remains closed even at a lower pressure setting, the user may determine that the malfunction is a complete blockage of the shunt and that the shunt needs to be surgically repaired.

Figure 8:
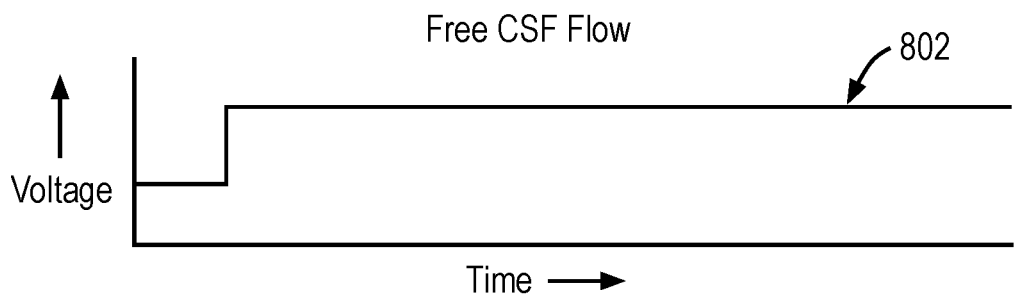
FIG. 8 illustrates a waveform indicative of a low valve threshold.

FIG. 8 illustrates a waveform indicative of a low valve threshold. In particular, waveform 802 illustrates a constant (non-pulsatile) voltage. This indicates that CSF pressure valve 214 is continuously open and therefore CSF is constantly flowing past pressure valve 214. A constant CSF flow indicates that the valve threshold setting may be too low and allowing an unnecessarily large amount of CSF to drain. The external device 502 would therefore display to the user that the valve threshold is low. Based on this information, the user can increase the pressure threshold of pressure valve 214 and take a second reading. If the second reading indicates a more pulsatile voltage comparable to control waveform 602, the user can verify it was the threshold setting that needed to be adjusted and that surgical repair is not necessary. If the reading remains the same, the user may determine that the malfunction is the pressure valve 214 and proceed with surgical intervention.

Figure 9:
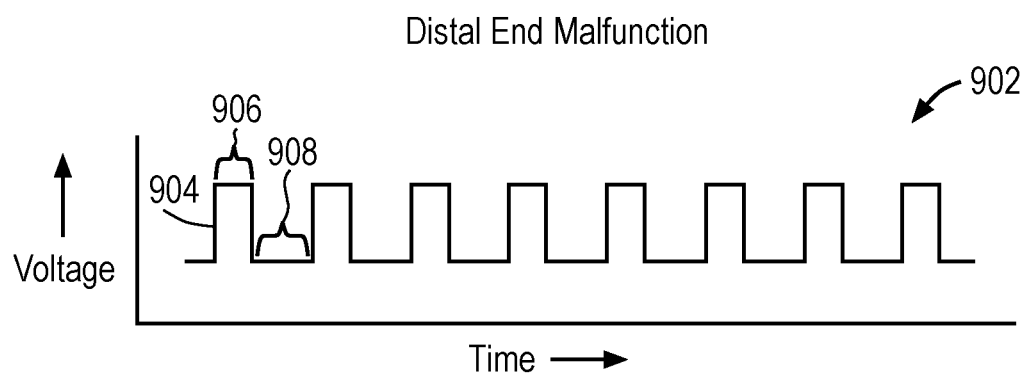
FIG. 9 illustrates a waveform indicative of a shunt having a distal end malfunction.

FIG. 9 illustrates a waveform indicative of a shunt having a distal end malfunction. In particular, waveform 902 illustrates a wave 904 having a wave period 906 less than that of the control waveform 602 and also a between wave period 908 less than that of the control waveform 602. In other words, there is a bottleneck at the region of shunt valve assembly 202 distal to sensor assembly 216. This bottleneck causes pressure to build up within the area of valve assembly 104 distal to pressure valve 214. Pressure valve 214 does not open unless the difference between a pressure at its proximal end and distal end is greater than the predetermined pressure valve threshold setting. If the pressure at the distal end of pressure valve is greater than a pressure at a proximal end of pressure valve 214, pressure valve 214 closes. Alternatively, if the pressure at the distal end is less than the pressure at the proximal end and the difference between the two is greater than the pressure threshold setting of pressure valve 214, pressure valve 214 opens. As such, in the case of a distal blockage, pressure valve 214 may initially open to allow CSF flow; the CSF quickly begins to build up at the distal end, thus rapidly increasing a pressure at the distal end of pressure valve 214 above the pressure at its proximal end. This causes pressure valve 214 to close and CSF flow past pressure valve 214 to stop. CSF, however, is still flowing into the proximal end of valve assembly 104 and building up at the proximal end of pressure valve 214. In turn, the distal blockage may not be a complete blockage therefore the pressure level distal to valve 214 may be slowly decreasing to the point where the difference between the proximal end pressure and distal end pressure of pressure valve 214 is once again greater than the threshold pressure value of pressure valve 214. Pressure valve 214 in turn opens, but again, only briefly before it closes again and prevents CSF flow past pressure valve 214, because the distal pressure continues to quickly build. As a result of these occurrences, waveform 902 having wave periods 906 (i.e., open valve periods) which are narrower (i.e., shorter duration) than that of control 602 and between wave periods 908 (i.e., closed valve periods) which are closer (i.e., shorter duration) than control 602.

Based on this information, the external device 502 would display to the user that the shunt distal end is malfunctioning. The care provider should therefore repair the anti-siphon member 218, distal valve tube 244 or possibly the distal catheter 108. Although the specific component within the distal end may not be identified, such information is not necessary for surgical intervention. In particular, regardless of which distal end component is malfunctioning, surgical repair of any of the components can be achieved by one incision at the distal end. Thus, identification of the specific component prior to surgery is not necessary. It is contemplated, however, that it may be possible to locate the specific component that is malfunctioning by taking additional readings. For example, the settings of valve 214 may be modified and further readings taken to further identify the point of malfunction.

Figure 10:
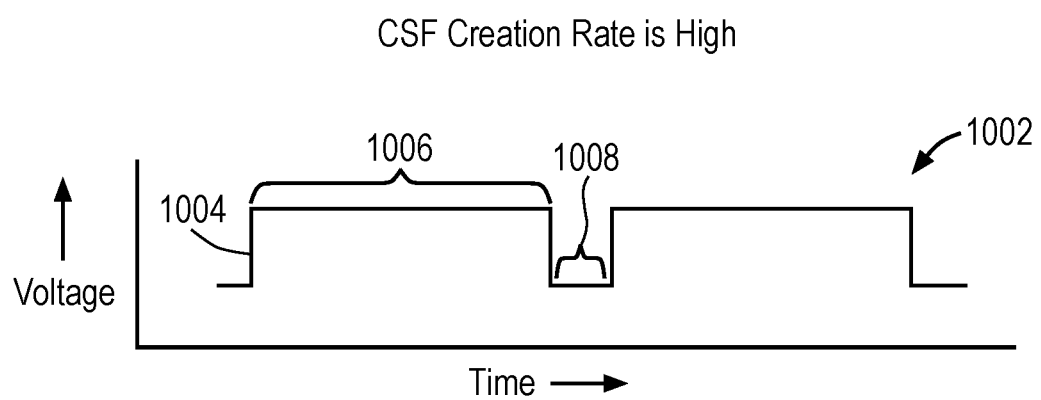
FIG. 10 illustrates a waveform indicative of a high CSF production rate.

FIG. 10 illustrates a waveform indicative of a high CSF production rate. In particular, waveform 1002 illustrates a wave 1004 having a wave period 1006 greater than that of the control waveform 602 and also a between wave period 1008 less than that of the control waveform 602. In other words, pressure valve 214 is remaining open for longer periods of time than that of the control and closing for shorter periods of time. This indicates a high CSF production rate because when the CSF production rate is high, CSF continues to flow into valve assembly 104 and to pressure valve 214. Once the pressure at pressure valve 214 is above the predetermined threshold value, pressure valve 214 opens to relieve the pressure but CSF continues to flow into valve assembly 104 thus requiring pressure valve 214 to remain open for a longer period of time to reduce the pressure below the threshold. Once the pressure is reduced below the threshold pressure level, pressure valve 214 closes but only for a short period of time before the pressure level increases again causing pressure valve 214 to open. As a result of these occurrences, waveform 1002 having wave periods 1006 (i.e., open valve periods) which are wider (i.e., longer duration) than that of control 602 and between wave periods 1008 (i.e., closed valve periods) which are closer (i.e., shorter duration) than control 602.

Based on these results, the external device 502 would display to the user that the CSF production rate is high. This indicates to the user that the pressure valve threshold level should be reduced to allow for draining of more CSF.

Figure 11:
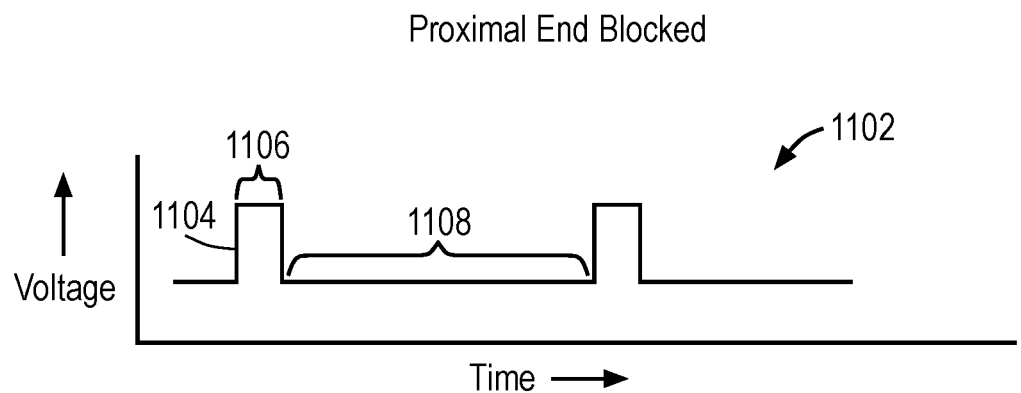
FIG. 11 illustrates a waveform indicative of a proximal end blockage.

FIG. 11 illustrates a waveform indicative of a proximal end blockage. In particular, waveform 1102 illustrates a wave 1104 having a wave period 1106 less than that of the control waveform 602 and a between wave period 1108 greater than that of the control waveform 602. In other words, pressure valve 214 is remaining open for shorter periods of time than that of the control and closing for longer periods of time. This indicates a proximal end blockage because when the proximal end is fully or partially blocked, there is no, or only a small amount in the case of a partial blockage, of CSF flow into valve assembly 104 and to pressure valve 214. It therefore takes a relatively long time for a pressure level proximal to pressure valve 214 to build to a level above the predetermined pressure threshold setting of pressure valve 214 and cause pressure valve 214 to open. Once pressure valve 214 does open, it requires a relatively short period of time for CSF to drain and cause the pressure to drop below the threshold level. As a result, waveform 1102 has wave periods 1106 (i.e., open valve periods) which are narrower (i.e., shorter duration) than that of control 602 and between wave periods 1108 (i.e., closed valve periods) which are longer (i.e., longer duration) than control 602.

Based on these results, the external device 502 would display to the user that there is a proximal end blockage. This indicates to the user that one of the components proximal to pressure valve 214 is in need of repair. For example, reservoir 210, one-way valve 208, proximal valve tube 242 or proximal catheter 106. Since the surgeon now knows the general location of malfunction, a single incision at the proximal end of valve assembly 104 can be made and any of the above-referenced proximal components accessed through the single incision for repair.

Figure 12:
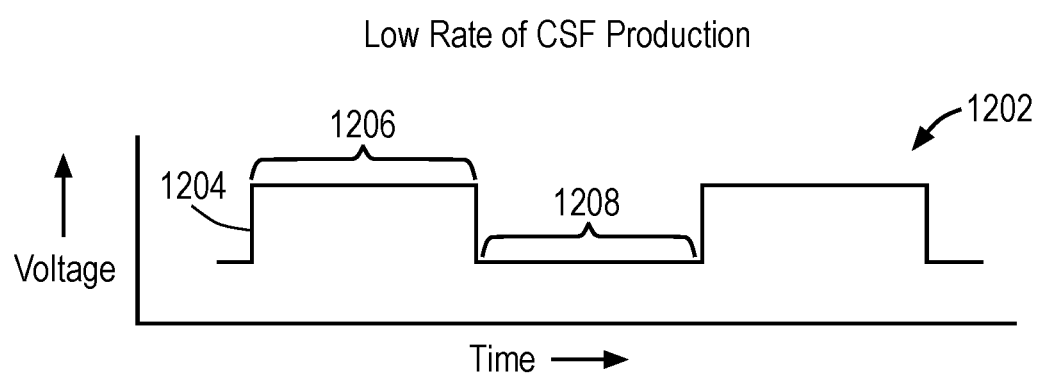
FIG. 12 illustrates a waveform indicative of a low rate of CSF production.

FIG. 12 illustrates a waveform indicative of a low rate of CSF production. In particular, waveform 1202 illustrates a wave 1204 having a wave period 1206 greater than that of the control waveform 602 and a between wave period 1208 greater than that of the control waveform 602. In other words, pressure valve 214 is remaining open for longer periods of time than that of the control and closing for longer periods of time. This indicates a low rate of CSF production. As a result, waveform 1202 has wave periods 1206 (i.e., open valve periods) which are longer (i.e., longer duration) than that of control 602 and between wave periods 1208 (i.e., closed valve periods) which are longer (i.e., longer duration) than control 602.

Based on these results, the external device 502 would display to the user that CSF production rate is low. This indicates to the user that the pressure threshold level of pressure valve 214 should be increased. The care provider may therefore increase the threshold level without the need for an invasive exploratory procedure.

Table 1 below illustrates each of the above-described algorithms and exemplary actions that could be taken in response to the readings displayed on external device 502.

TABLE 1

| Algorithm | Period between waves (pressure valve closed) | Period of wave (pressure valve open) | Shunt Condition | Action |
|---|---|---|---|---|
| 1 (FIG. 6) | Same as control | Same as control | Properly functioning | None |
| 2 (FIG. 7) | No wave | No wave | Complete blockage; or no CSF production beyond pressure valve threshold | Decrease pressure valve threshold and take second reading |
| 3 (FIG. 8) | None | Greater than control | Low pressure valve threshold setting | Increase pressure valve threshold |
| 4 (FIG. 9) | Less than control | Less than control | Distal end malfunction | Repair distal end (e.g. anti-siphon member and/or distal catheter) |
| 5 (FIG. 10) | Less than control | Greater than control | High CSF production rate | Decrease pressure valve threshold |
| 6 (FIG. 11) | Greater than control | Less than control | Proximal end malfunction | Repair proximal end (e.g. reservoir, one-way valve, proximal valve, or proximal catheter) |
| 7 (FIG. 12) | Greater than control | Greater than control | Low CSF production rate | Increase pressure valve threshold |

Figure 13:
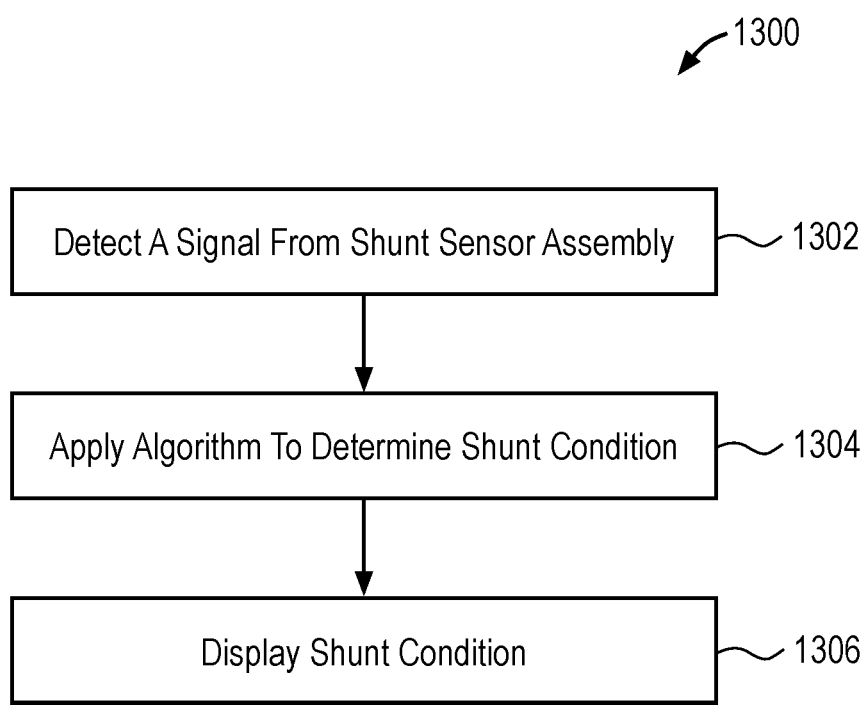
FIG. 13 illustrates one embodiment of a method for transdermally detecting a shunt condition.

One representative method for transdermally detecting a shunt condition is illustrated in FIG. 13. In one embodiment, the external device is used to transdermally detect a signal from the shunt sensor assembly (block 1302). The signal may be output by the previously described sensor assembly which detects a flow of fluid through the shunt and generates a signal indicative of a period of fluid flow. Once the signal is detected, any one or more of the previously described algorithms is applied to determine the shunt condition (block 1304). For example, the external device, or a display device coupled to the external device, may include a signal processing program that can process the signal according to the previously discussed algorithms to determine the shunt condition. The shunt condition is displayed to the user on the display (block 1306). Based on the displayed shunt condition, the user can determine the appropriate course of action.

Figure 14:
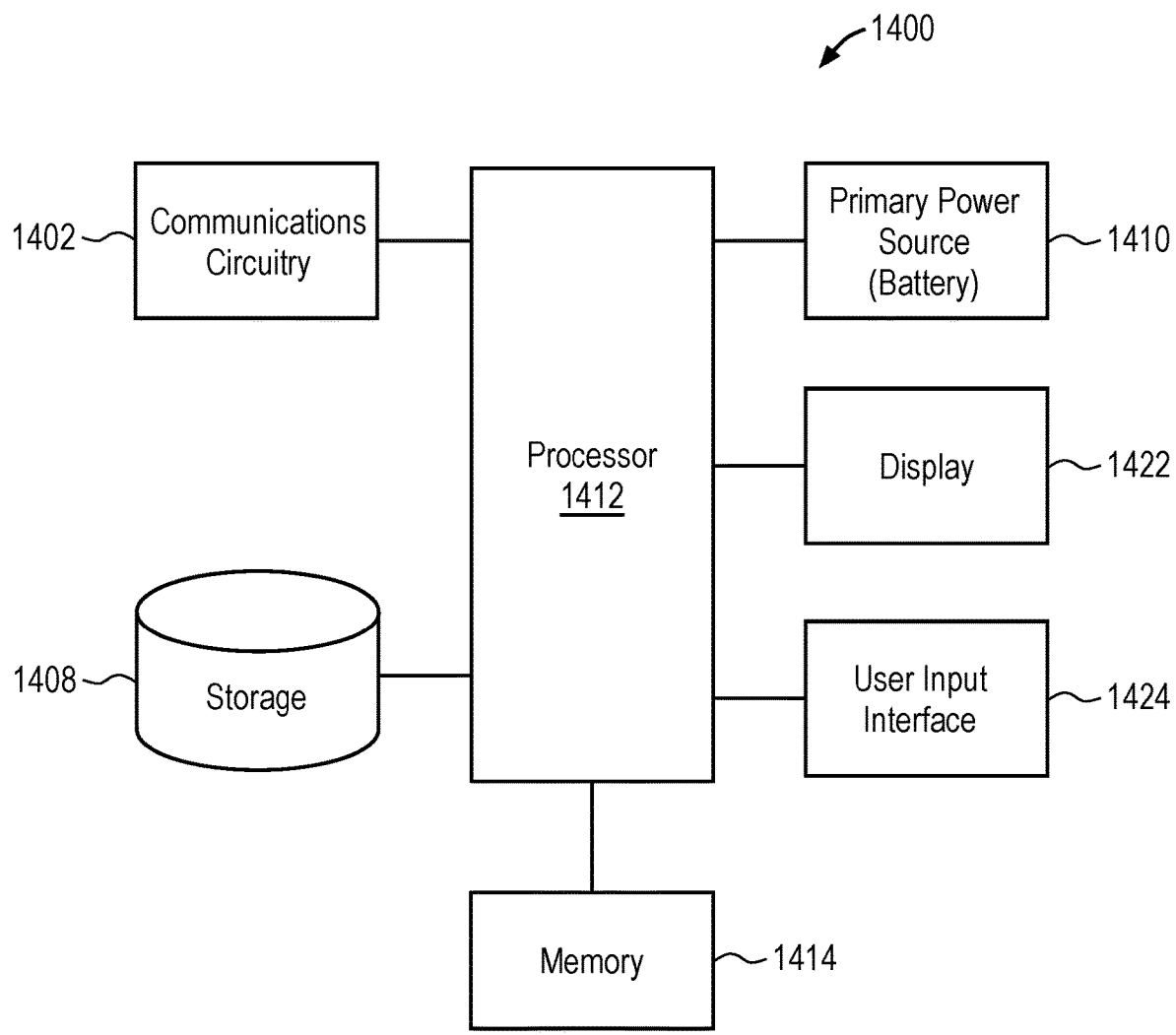
FIG. 14 illustrates a block diagram of some of the constituent components of an embodiment of an external device.

FIG. 14 illustrates a block diagram of some of the constituent components of an embodiment of an external device within which the previously described signal and algorithm can be processed. Device 1400 may be any one of several different types of electronic devices that can be easily held in the user's hand during normal use. In particular, the device 1400 may be any mobile device, such as a cellular phone, a smart phone, or a tablet-like portable computer. In one embodiment, device 1400 is an external device such as external device 502 illustrated in FIG. 5B.

In this aspect, external device 1400 includes a processor 1412 that interacts with storage 1408, memory 1414, display 1422, and user input interface 1424. Main processor 1412 may also interact with communications circuitry 1402 and primary power source 1410. The various components of the external device 1400 may be digitally interconnected and used or managed by a software stack being executed by the processor 1412. Many of the components shown or described here may be implemented as one or more dedicated hardware units and/or a programmed processor (software being executed by a processor, e.g., the processor 1412).

The processor 1412 controls the overall operation of the device 1400 by performing some or all of the operations of one or more applications or operating system programs implemented on the device 1400, by executing instructions for it (software code and data) that may be found in the storage 1408. The processor may, for example, drive the display 1422 and receive user inputs through the user input interface 1424 (which may be integrated with the display 1422 as part of a single, touch sensitive display panel). In addition, processor 1412 may process the signal received from the secondary induction coil positioned within external device 1400 according to the previously described algorithms.

Storage 1408 provides a relatively large amount of "permanent" data storage, using nonvolatile solid state memory (e.g., flash storage) and/or a kinetic nonvolatile storage device (e.g., rotating magnetic disk drive). Storage 1408 may include both local storage and storage space on a remote server. Storage 1408 may store and record data as well as software components that control and manage, at a higher level, the different functions of the device 1400.

In addition to storage 1408, there may be memory 1414, also referred to as main memory or program memory, which provides relatively fast access to stored code and data that is being executed by the processor 1412. Memory 1414 may include solid state random access memory (RAM), e.g., static RAM or dynamic RAM. There may be one or more processors, e.g., processor 1412, that run or execute various software programs, modules, or sets of instructions (e.g., algorithms 1-7 of Table 1) that, while stored permanently in the storage 1408, have been transferred to the memory 1414 for execution, to perform the various functions described above.

The device 1400 may include communications circuitry 1402. Communications circuitry 1402 may include components used for wired or wireless communications, such as two-way conversations and data transfers. For example, communications circuitry 1402 may include Wi-Fi communications circuitry so that the user of the device 1400 may transfer data through a wireless local area network.

Device 1400 also includes primary power source 1410, such as a built in battery, as a primary power supply. Alternatively, power source 1410 may derive power from an alternating current (AC) power supply in a building, such as through a cord, Wi-Fi signal, solar source or other external power source.

In still further embodiments, the external device may be a non-mobile external device, for example, a desk top computer, desk top monitor or television. Similar to device 1400, the non-mobile external device may include a processor that interacts with, a storage unit, memory unit, display, user input interface and communications circuitry. The non-mobile external device may further interact with a probe type device having secondary induction coil which can be used to receive the signal from the primary induction coil positioned within the valve assembly. The various components of the external device may be digitally interconnected and used or managed by a software stack being executed by the main processor. Many of the components shown or described here may be implemented as one or more dedicated hardware units and/or a programmed processor (software being executed by a processor, e.g., the main processor).

Figure 15A:
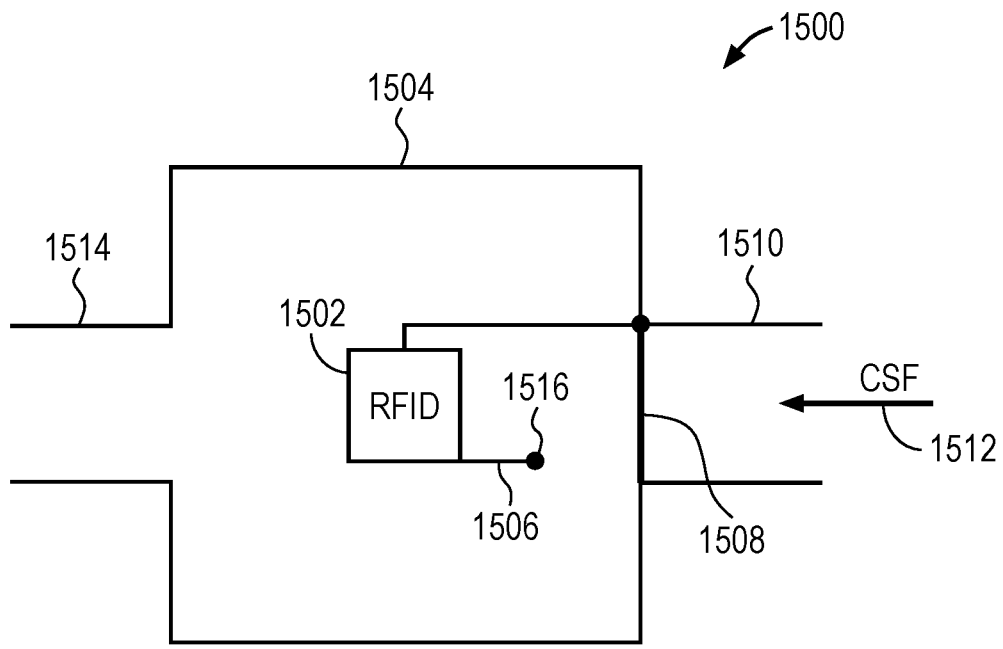
FIG. 15A illustrates one embodiment of a pressure valve having a sensor assembly integrated therein.
Figure 15B:
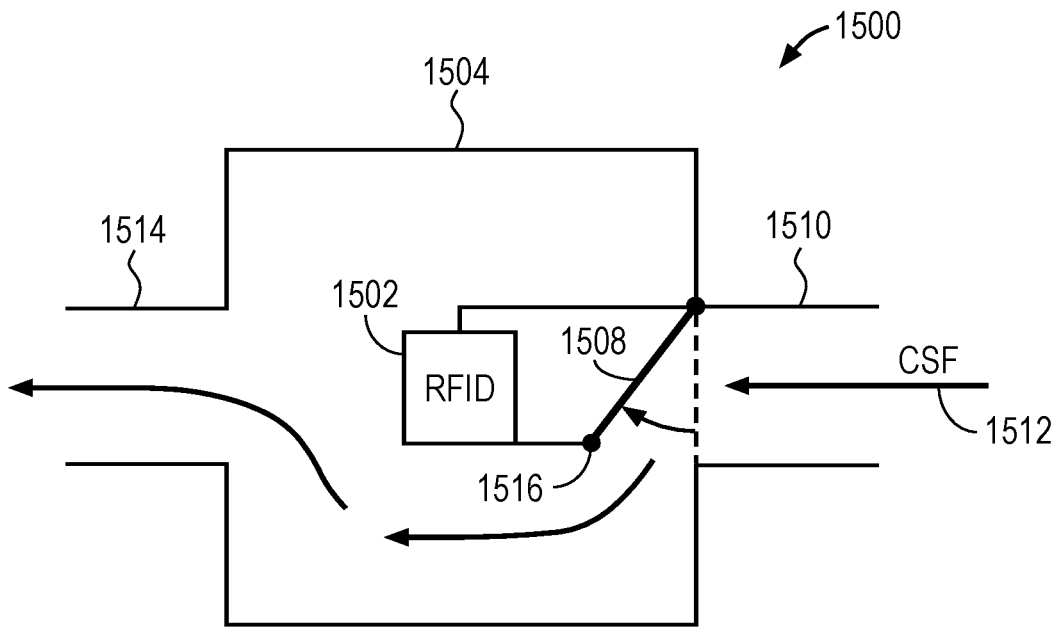
FIG. 15B illustrates one embodiment of the pressure valve of FIG. 15A.

FIG. 15A and FIG. 15B illustrate an embodiment of a pressure valve having a sensor assembly integrated therein. Pressure valve 1500 may be one example of the pressure valve 214 which can be integrated within shunt 102 as previously described in reference to, for example, FIG. 2 and FIG. 3. In this embodiment, pressure valve 1500 may include a sensor integrated therein such that a separate sensor assembly (e.g. sensor assembly 216) can be omitted. Representatively, pressure valve 1500 may include a sensor such as a passive radio frequency identification (RFID) tag 1502 positioned within housing 1504 of valve 1500. Tag 1502 is used to communicate the status of the shunt externally. Representatively, tag 1502 can be powered by an external device having an active reader (e.g. device 502 having an active reader or any of the other previously discussed external devices) configured to broadcast at the excitation frequency of tag 1502. The active reader transmits interrogator signals and also receives authentication replies (i.e. communications) from tag 1502. Tag 1502 includes broadcasting circuitry 1506 which is broken (or open) when the valve gate 1508 is in the closed position (i.e. no CSF is flowing through valve 1500) and closed when valve gate 1508 is in the open position (i.e. CSF is flowing through valve 1500). Valve gate 1508 may be pressure sensitive such that pressure on valve gate 1508 from CSF flow in the direction of arrow 1512 causes the valve gate 1508 to either open (when the pressure is great enough) or close (when the pressure is not great enough). The status and/or malfunction of the shunt in which pressure valve 1500 is incorporated (e.g. shunt 102) can be determined based on the RFID tag signal indicating whether the valve gate 1508 is open (CSF flow) or closed (no CSF flow) using any one or more of the previously discussed algorithms.

For example, in one embodiment, valve gate 1508 may be a tension spring connected to an electrical circuit of tag 1502. When the spring is displaced due to flow of CSF in the direction of arrow 1512 (as illustrated in FIG. 15B) through the valve input tube 1510, the spring contacts an electrical contact 1516 of tag 1502, closing the broadcasting circuit of tag 1502 and allowing its signal to be read by the external reader. When the signal is output from tag 1502 to the reader, the reader (or an associated computing device) interprets this information to mean that valve gate 1508 is open and CSF is flowing through the valve. FIG. 15A illustrates valve gate 1508 in the closed position such that CSF cannot flow into valve housing 1504, and in turn no signal is output from tag 1502 to the reader. When no signal is output from tag 1502 to the reader, the external reader device (or an associated computing device) interprets this information to mean that valve gate 1508 is closed and no CSF is flowing through valve 1500. Any one or more of the previously discussed algorithms in Table 1 (illustrated in FIGS. 6-12) are then used to determine a malfunction and/or status of the shunt.

Figure 16A:
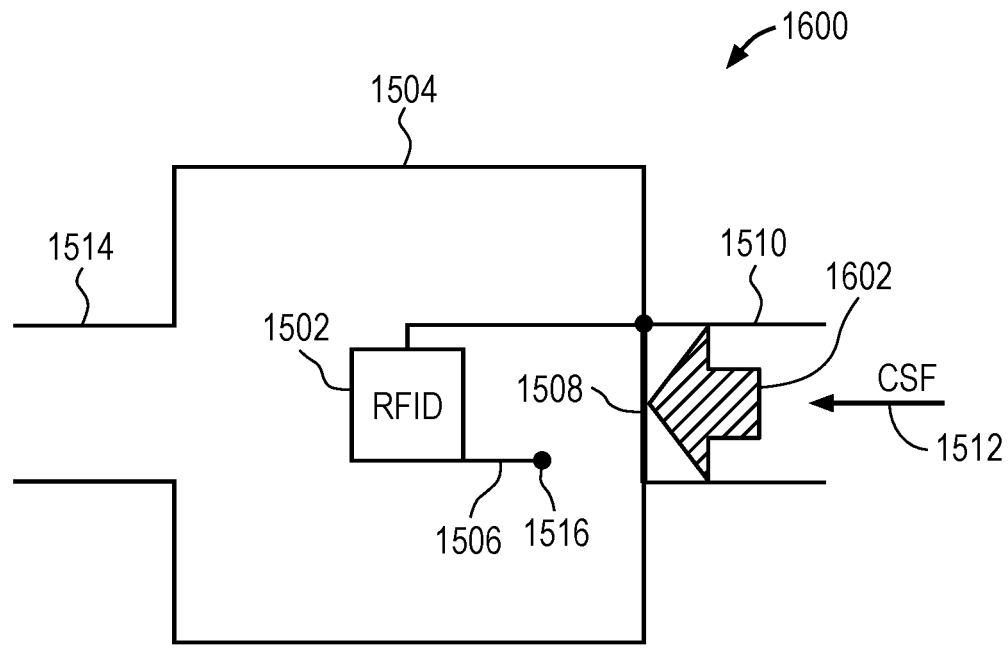
FIG. 16A illustrates another embodiment of a pressure valve having a sensor assembly integrated therein.
Figure 16B:
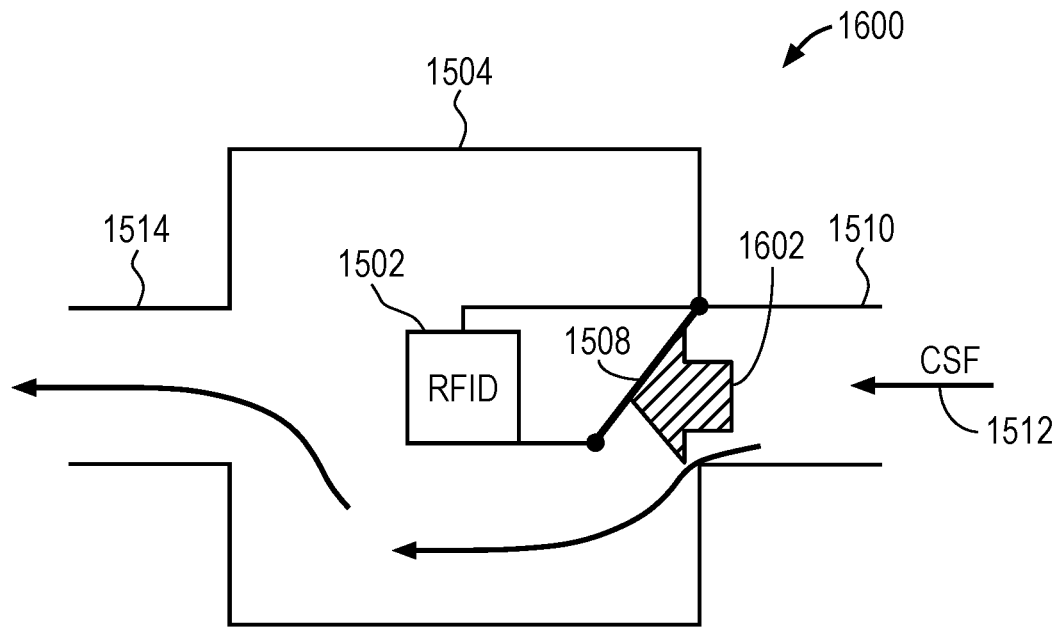
FIG. 16B illustrates one embodiment of the pressure valve of FIG. 16A.

FIG. 16A and FIG. 16B illustrate another embodiment of a pressure valve having a sensor assembly integrated therein. Valve 1600 is substantially similar to valve 1500 described in reference to FIG. 15A-15B except in this embodiment, valve 1600 is a ball valve having a ball 1602, which presses against valve gate 1508, and in turn, opens valve gate 1508 when CSF flow causes a sufficient pressure against ball 1602. Representatively, as illustrated in FIG. 16A, ball 1602 is in front of valve gate 1508 such that CSF flow in the direction of arrow 1512 causes ball 1602 to press against valve gate 1508. Valve gate 1508, however, remains closed because there is insufficient pressure to open it. As previously discussed, when valve gate 1508 is closed, the circuit of RFID tag 1502 is open and therefore tag 1502 does not output a signal to the external reader device. Once a pressure against the ball 1602 due to CSF flow reaches a threshold level, however, the pressure of ball 1602 against valve gate 1508 causes valve gate 1508 to open, and in turn, complete the circuit with RFID tag 1502 such that a signal is output to the external reader device.

Each of pressure valve 1500 and 1600, and any of the other pressure valves disclosed herein, may be programmable valves in which the pressure setting of the gate can be changed or fixed valves having a fixed pressure setting. In addition, it should be understood that pressure valves 1500 and 1600 provide a unique advantage in that since they have an RFID tag sensor integrated therein, in addition to being able to be monitored externally, they can be monitored from a distance (i.e. several meters) and no alignment or direct contact of the reader device with the patient and/or shunt is required. It is further to be understood that although tag 1502 is described as a passive RFID tag, it is contemplated that an active RFID tag may be used and the reader may be a passive reader or an active reader.

Figure 17:
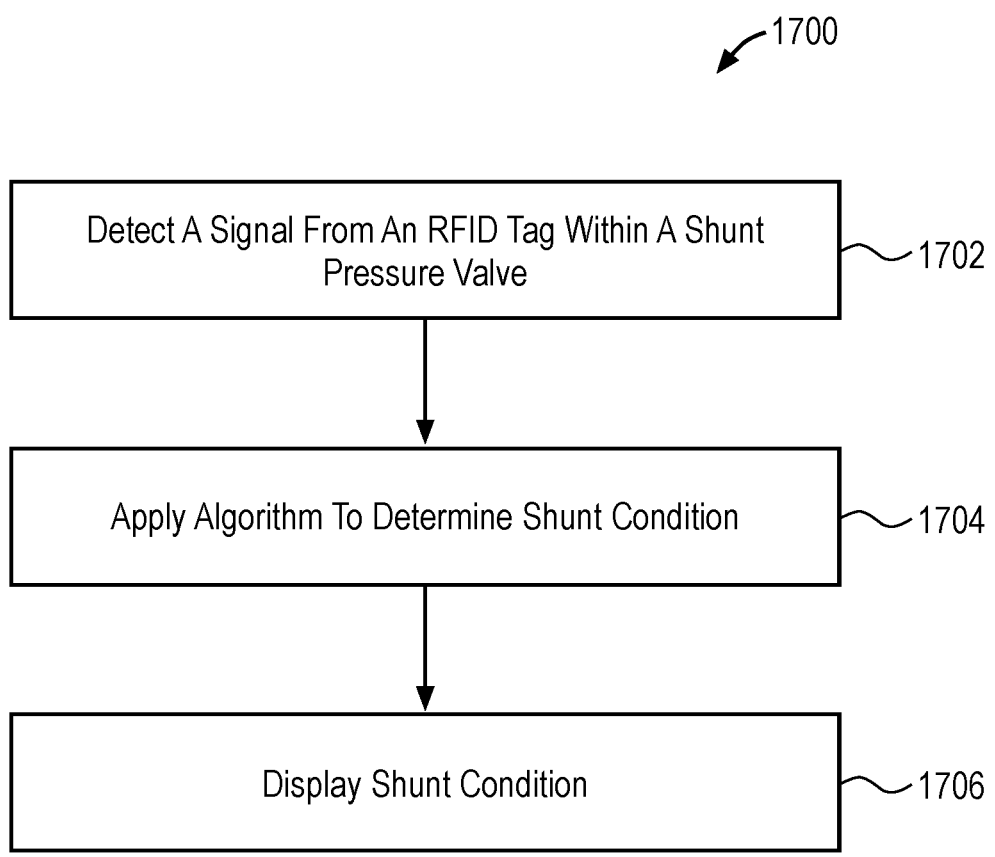
FIG. 17 represents another method for transdermally detecting a shunt condition.

FIG. 17 represents another method for transdermally or non-invasively detecting a shunt condition. In one embodiment, an external device (e.g. mobile device having an RFID tag reader or patch) is used to transdermally detect a signal from an RFID tag integrated within a shunt pressure valve (block 1702). A signal indicating whether the pressure valve is open or closed may be output by the RFID tag. Once the signal is detected, any one or more of the previously described algorithms of Table 1 is applied to determine the shunt condition (block 1704). For example, the external device, or a display device coupled to the external device, may include a signal processing program that can process the signal according to the previously discussed algorithms to determine the shunt condition. The shunt condition is displayed to the user on the display (block 1706). Based on the displayed shunt condition, the user can determine the appropriate course of action.

It is further to be understood that the external device, such as device 502, for performing the operations herein may be specially constructed for the required purposes or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs and magnetic-optical disks, read-only memories (ROMs), random access memories (RAMs), EPROMs, EEPROMs, magnetic or optical cards, Flash memory devices including universal serial bus (USB) storage devices (e.g., USB key devices) or any type of media suitable for storing electronic instructions, each of which may be coupled to a computer system bus.

The algorithms and displays presented herein are not inherently related to any particular computer or other apparatus. Various general purpose systems may be used with programs in accordance with the teachings herein or it may prove convenient to construct a more specialized device to perform the described method. In addition, the invention is not described with reference to any particular programming language. It will be appreciated that a variety of programming languages may be used to implement the teachings of the invention as described herein.

A computer readable medium includes any mechanism for storing information in a form readable by a computer. For example, a computer readable medium includes read only memory ("ROM"), random access memory ("RAM"), magnetic disk storage media; optical storage media, flash memory devices or other type of machine-accessible storage media.

In the preceding detailed description, specific embodiments are described. It will, however, be evident that various modifications and changes may be made thereto without departing from the broader spirit and scope of the claims. The specification and drawings are, accordingly, to be regarded in an illustrative rather than restrictive sense.

What is claimed is:

1. A method for detecting a condition of an implantable shunt comprising:
   detecting a flow of fluid through a pressure valve within an implantable shunt;
   generating a signal indicative of the flow of fluid based on the detecting, wherein the signal indicates at least one of a first period of time corresponding to a period of time the pressure valve is in an open position and a second period of time corresponding to a period of time the pressure valve is in a closed position, wherein the signal is generated by a single sensor assembly based on an opening or closing of the pressure valve, wherein the sensor assembly comprises (1) a mechanically actuated rotor coupled to a generator, wherein the rotor rotates as fluid flows through the pressure valve and the generator generates a signal indicative of the flow of fluid through the rotor or (2) circuitry coupled to the pressure valve such that when the pressure valve is open, the circuitry of the sensor assembly is closed, and when the pressure valve is closed, the circuitry is open; and
   outputting the signal to a device operable to determine, from the signal, a condition of the implantable shunt.

2. The method of claim 1 wherein the condition is a malfunction of the implantable shunt.

3. The method of claim 2 further comprising:
   identifying a location of the malfunction from the signal.

4. The method of claim 3 wherein the location of the malfunction is at the pressure valve.

5. The method of claim 3 wherein the location of the malfunction is at a distal portion of the implantable shunt.

6. The method of claim 3 wherein the location of the malfunction is at a proximal portion of the implantable shunt.

7. The method of claim 1 wherein when the signal indicates the pressure valve is continuously closed, the condition is either a complete blockage of the implantable shunt or a fluid flow rate below a pressure threshold of the pressure valve.

8. The method of claim 1 wherein when the signal indicates the pressure valve is continuously open, the condition is a low threshold pressure of the pressure valve and the threshold pressure is increased.

9. The method of claim 1 wherein when the first period of time and the second period of time are the same as a control signal, the condition is a properly functioning implantable shunt.

10. The method of claim 1 wherein when the first period of time and the second period of time are less than a control signal, the condition is a malfunction at a distal end of the implantable shunt.

11. The method of claim 1 wherein when the first period of time is greater than a control signal and the second period of time is less than the control signal, the condition is a high fluid production rate and a threshold pressure of the pressure valve is decreased.

12. The method of claim 1 wherein when the first period of time is less than a control signal and the second period of time is greater than the control signal, the condition is a malfunction at a proximal end of the implantable shunt.

13. The method of claim 1 wherein when the first period of time and the second period of time are greater than a control signal, the condition is a low fluid production rate and a threshold pressure of the pressure valve is increased.

14. The method of claim 1 wherein the signal is generated by a mechanically actuated sensor assembly comprising the rotor and the generator.

15. The method of claim 1 wherein the signal is generated by a radio-frequency identification tag comprising the circuitry.

16. The method of claim 1 wherein the device is an external device comprising a processor for determining the condition of the implantable shunt.

17. The method of claim 1 wherein the device is electrically coupled to a lead for continuous monitoring of the condition of the implantable shunt.

18. A shunt system comprising:
- an implantable housing having a proximal end and a distal end, wherein a fluid inlet port is formed in the proximal end and a fluid outlet port is formed in the distal end;
- a pressure sensitive valve contained within the housing at a position between the proximal end and the distal end, the pressure sensitive valve capable of controlling a flow of fluid between the fluid inlet port and the fluid outlet port;
- a sensor assembly coupled to the pressure sensitive valve, wherein the sensor assembly comprises a radio frequency identification tag having circuitry that is electrically coupled to a valve gate of the pressure sensitive valve and is operable to detect the flow of fluid and output a signal indicative of a period of fluid flow through the implantable housing based on the detecting, wherein the circuitry of the radio frequency identification tag is coupled to the valve gate such that when the valve gate is open, the circuitry of the radio frequency identification tag is closed, and when the valve gate is closed, the circuitry of the radio frequency identification tag is open, and wherein the signal indicates at least one of a first period of time corresponding to a period of time the valve gate is open and a second period of time corresponding to a period of time the valve gate is closed; and
- a processor operable to determine, based on the signal, a malfunction of the shunt.

19. The shunt system of claim 18 wherein the signal indicative of the period of fluid flow is output to an external reading device having a radio frequency identification reader, and the processor is associated with the external reading device.

* * * * *